United States Patent
Rose et al.

(10) Patent No.: US 6,576,595 B1
(45) Date of Patent: Jun. 10, 2003

(54) XANTHONE DERIVATIVES, PROCESSES FOR THEIR PREPARATION AND THEIR USE FOR CONTROLLING HARMFUL FUNGI, AND COMPOSITIONS COMPRISING THESE DERIVATIVES

(75) Inventors: Ingo Rose, Mannheim (DE); Jordi Tormo i Blasco, Limburgerhof (DE); Markus Gewehr, Kastellaun (DE); Wassilios Grammenos, Ludwigshafen (DE); Bernd Müller, Frankenthal (DE); Joachim Rheinheimer, Ludwigshafen (DE); Peter Schäfer, Ottersheim (DE); Frank Schieweck, Hessheim (DE); Thomas Grote, Wachenheim (DE); Andreas Gypser, Mannheim (DE); Eberhard Ammermann, Heppenheim (DE); Gisela Lorenz, Hambach (DE); Reinhard Stierl, Mutterstadt (DE); Siegfried Strathmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/251,783

(22) Filed: Sep. 23, 2002

(30) Foreign Application Priority Data

Sep. 21, 2001 (DE) .......................... 101 46 706

(51) Int. Cl.$^7$ .......................... A01N 43/16; A01N 43/02
(52) U.S. Cl. .................. 504/292; 504/288; 549/16; 549/390
(58) Field of Search ................... 514/437, 455; 504/288, 292; 549/16, 390

(56) References Cited

U.S. PATENT DOCUMENTS 4,661,595 A 4/1987 Avár .......................... 546/89

FOREIGN PATENT DOCUMENTS

| CA | 2153791 | 8/1994 |
|---|---|---|
| DE | 43 01 424 | 7/1994 |
| EP | 0 507 039 | 10/1992 |
| WO | WO 97/34482 | 9/1997 |

OTHER PUBLICATIONS

Kato et al. "Synthesis of 1–Hydroxy–4, 6–dimethoxy–8–methylxanthone" Heterocycles vol. 5 (1976) pp. 167–170.

Primary Examiner—Amelia Owens
(74) Attorney, Agent, or Firm—Keil & Weinkauf

(57) ABSTRACT

Xanthone derivatives of the formula I

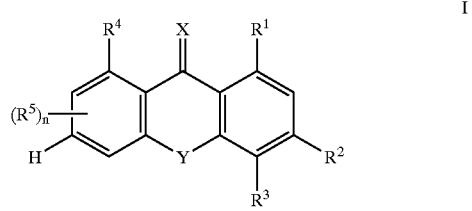

where the index and the variables are as defined below:

n is 0, 1 or 2;

$R^1$ is alkyl or haloalkyl;

$R^2, R^3$ are alkoxy, alkenyloxy or alkynyloxy, or $R^2$ and $R^3$ together form an unsubstituted or substituted oxyalkyleneoxy group;

$R^4$ is halogen, cyano, hydroxyl, amino, mercapto, alkyl, haloalkyl, alkoxy, haloalkoxy, alkylthio, haloalkylthio, alkylcarbonyloxy or alkylcarbonylthio;

$R^5$ is a group $R^4$, where the groups $R^5$ may be different if n=2;

X, Y are oxygen or sulfur;

Processes for preparing these compounds, compositions comprising them and their use for controlling phytopathogenic harmful fungi are described.

9 Claims, No Drawings

XANTHONE DERIVATIVES, PROCESSES FOR THEIR PREPARATION AND THEIR USE FOR CONTROLLING HARMFUL FUNGI, AND COMPOSITIONS COMPRISING THESE DERIVATIVES

The present invention relates to xanthone derivatives of the formula I

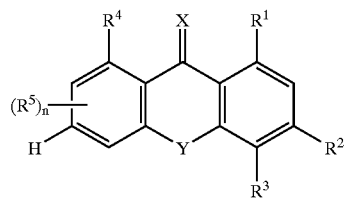

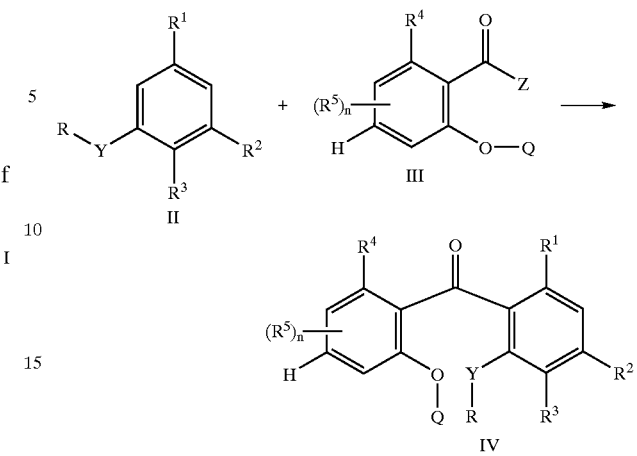

where the index and the variables are as defined below:

n is 0, 1 or 2;

$R^1$ is $C_1$–$C_4$-alkyl or $C_1$–$C_4$-haloalkyl;

$R^2$, $R^3$ independently of one another are hydrogen, $C_1$–$C_6$-alkoxy, $C_3$–$C_6$-alkenyloxy or $C_3$–$C_6$-alkynyloxy, or $R^2$ and $R^3$ together form an oxy-$C_1$–$C_4$-alkyleneoxy group which is unsubstituted or substituted by 1 to 4 of the following radicals: halogen, cyano, hydroxyl or $C_1$–$C_4$-alkyl;

$R^4$ is halogen, cyano, hydroxyl, amino, mercapto, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyloxy or $C_1$–$C_4$-alkylcarbonylthio;

$R^5$ is a group $R^4$, where the groups $R^5$ may be different if n=2;

X, Y independently of one another are oxygen or sulfur.

Moreover, the invention relates to processes for preparing these compounds, to compositions comprising them and to their use for controlling harmful fungi.

DE-A 4301424 discloses azaxanthones having herbicidal action.

An action of xanthone derivatives against phytopahtlogenic fungi has hitherto not been described in the prior art.

It is an object of the present invention to provide novel compounds having potent activity against phytopathogenic harmful fungi.

We have found that this object is achieved by the compounds defined at the outset. Moreover, we have found processes for their preparation, compositions comprising them and their use, and methods for controlling harmful fungi using the compounds I.

The compounds I can be obtained by different routes. Advantageously, the starting materials used are alkylbenzene derivatives of the formula II in which R is a $C_1$–$C_4$-alkyl group and salicylic acid derivatives of the formula III in which Q is a protective group, in particular a protective group which can be removed under alkaline conditions, such as, for example, hydrogen or alkylcarbonyl, and Z is halogen, alkoxy or hydroxyl [cf. T. W. Greene, Protective Groups in Organic Chemistry, J. Wiley & Sons, 1991, pp. 10–142].

The acylation of II to IV is usually carried out at temperatures of from −78° C. to 150° C., preferably from 0° C. to 100° C., in an inert organic solvent in the presence of an inorganic or organic acid, a Lewis acid or a dehydrating agent, such as, for example, $P_2O_5$ or $POCl_3$ [cf. Organikum, 20th edition, pp. 359–363, Joh. A. Barth Verlag, Heidelberg and Leipzig (1996)].

Suitable solvents are aliphatic hydrocarbons, aromatic hydrocarbons, such as nitrobenzene, halogenated hydrocarbons, such as methylene chloride, chloroform and chlorobenzene, ethers, nitriles, ketones, and also dimethyl sulfoxide, dimethylformamide and dimethylacetamide. Preference is given to nitrobenzene and halogenated hydrocarbons, particularly preferably dichloromethane. It is also possible to use mixtures of the solvents mentioned.

Suitable for use as acids and acidic catalysts are inorganic acids, such as hydrofluoric acid, hydrochloric acid, hydrobromic acid, sulfuric acid and perchloric acid, Lewis acids, such as boron trifluoride, aluminum trichloride, iron(III) chloride, tin(IV) chloride, titanium(IV) chloride and zinc(II) chloride, and also organic acids, such as formic acid, acetic acid, propionic acid, oxalic acid, toluenesulfonic acid, benzenesulfonic acid, camphorsulfonic acid, citric acid, trifluoromethanesulfonic acid and trifluoroacetic acid, inorganic acid anhydrides, such as phosphorus pentoxide, polyphosphoric acid and phosphorus oxychloride.

The acids are generally employed in catalytic amounts; however, they can also be employed in up to equimolar amounts, in excess or, if appropriate, as solvent.

The starting materials are generally reacted with one another in equimolar amounts. In terms of yield, it may be advantageous to employ an excess of II, based on III.

The starting materials II are known from the literature [Liebigs Ann. Chem. (1969), 220; JACS 113 (1991), pp. 8516–8518] or they can be prepared in accordance with the literature cited.

The protective group Q is introduced into the salicylic acid derivatives III following methods known from the literature [cf. T. W. Green, Protective Groups in Organic Chemistry, J. Wiley & Sons, 1991, pp. 10–142]. Suitable protective groups are, in general, groups which can be removed under alkaline conditions, such as $C_1$–$C_6$-alkylcarbonyl or hydrogen, in particular the pivaolyl group.

The cyclization of compounds IV to the xanthones of the formula I in which X is oxygen (formula Ia) is generally carried out at temperatures of from −78° C. to 150° C., preferably from 0° C. to 50° C., in an inert solvent in the presence of a base [cf. Org. Prep. Proceed. Int., 10 (1978), 79.

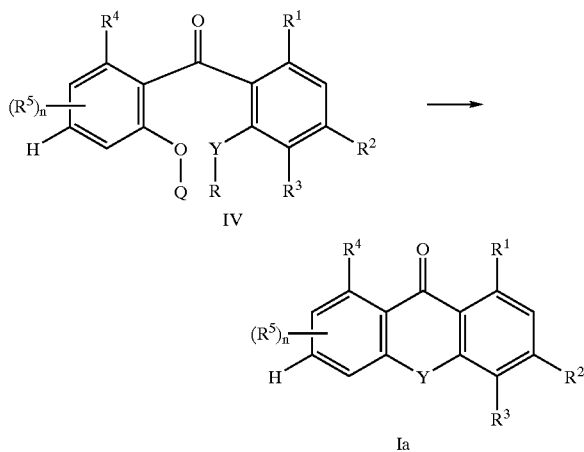

Suitable solvents are water, aliphatic hydrocarbons, aromatic hydrocarbons, halogenated hydrocarbons, ethers, nitriles, ketones, alcohols, such as methanol, ethanol, n-propanol, isopropanol, n-butanol and tert-butanol, and also dimethyl sulfoxide, dimethylformamide and diemthylacetamide, particularly preferably $C_1$–$C_5$-alcohol/water mixtures. It is also possible to use mixtures of the solvents mentioned.

Suitable bases are, in general, inorganic compounds, such as alkali metal and alkaline earth metal hydroxides, alkali metal and alkaline earth metal oxides, alkali metal and alkaline earth metal hydrides, such as lithium hydride, sodium hydride, potassium hydride and calcium hydride, alkali metal amides, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, alkylmagnesium halides and also alkali metal and alkaline earth metal alkoxides and dimethoxymagnesium, moreover organic bases, for example tertiary amines, pyridine, substituted pyridines and also bicyclic amines. Preference is given to alkali metal hydroxides, alkali metal carbonates, alkali metal bicarbonates and alkali metal hydrides. Particular preference is given to NaOH, KOH, $NaHCO_3$ and $Na_3CO_3$.

The removal of the protective group from IV and the cyclization can also be carried out in two steps. The removal of the protective group is preferably carried out at temperatures of from –50° C. to 100° C., preferably from 0° C. to 50° C., in an inert solvent, preferably in alcohol/water mixtures, in the presence of a base.

Suitable bases are, in general, inorganic compounds, such as alkali metal and alkaline earth metal carbonates, such as lithium carbonate, potassium carbonate and calcium carbonate, and also alkali metal bicarbonates, such as sodium bicarbonate. Particular preference is given to sodium bicarboante.

The cyclization of the compounds IV in which Q is hydrogen is usually carried out at temperatures of from 0° C. to 150° C., preferably from 50° C. to 150° C., in an inert organic solvent in the presence of a base [cf. Org. Prep. Proceed. Int. 10 (1978), 79].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisol and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also N-methylpyrrolidone (NMP), dimethyl sulfoxide (DMSO), dimethylformamide (DMF) and dimethylacetamide (DMA), particularly preferably methanol, ethanol, DMSO and NMP. It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, alkali metal and alkaline earth metal alkoxides, alkali metal and alkaline earth metal carbonates and also alkali metal bicarbonates, such as sodium bicarbonate. Particular preference is given to potassium hydroxide.

The bases are generally employed in equimolar amounts or in excess.

Xanthones I in which X and Y are oxygen (formula IA) can also be obtained from o-halobenzoic acid derivatives IIIa, by the following route:

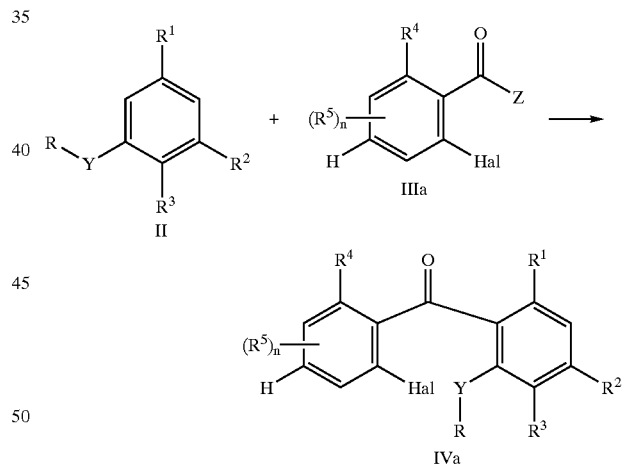

The compounds IVa are obtainable from alkylbenzene derivatives of the formula II and benzoic acid derivatives of the formula IIIa in which Hal is halogen and in particular chlorine and the other variables are as defined in formula III, under the conditions described for the acylation of II with III. The acylation of II with IIIa is preferably carried out in the presence of $P_2O_5$ or polyphosphoric acid, if Z is hydroxyl. If Z is halogen, the reaction is carried out in the presence of $AlCl_3$.

If compounds I are to be synthesized in which $R^5$ is halogen, the group $R^5$ can be introduced at the stage of the compounds IVa.

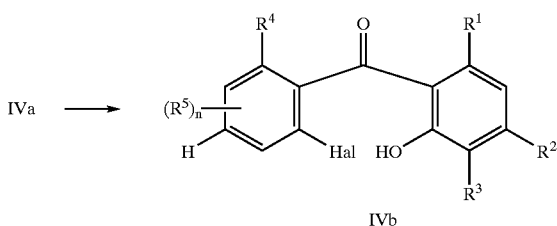

The conversion of the compounds IVa into the hydroxyl compounds IVb is usually carried out at temperatures of from −78° C. to 100° C., preferably from 0° C. to 50° C., in an inert organic solvent in the presence of a Lewis acid [cf. T. W. Greene, Protective Groups in Organic Chemistry, J. Wiley & Sons, 1991, pp. 146–149].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisol and tetrahydrofuran, nitriles, ketones, alcohols, and also dimethyl sulfoxide, dimethylformamide and dimethylacetamide, particularly preferably tetrahydrofuran. It is also possible to use mixtures of the solvents mentioned.

Suitable Lewis acids are, in general, main group and transition group halides, such as $BF_3$, $AlCl_3$, $FeCl_3$, $SnCl_4$, $TiCl_4$ or $ZnCl_2$.

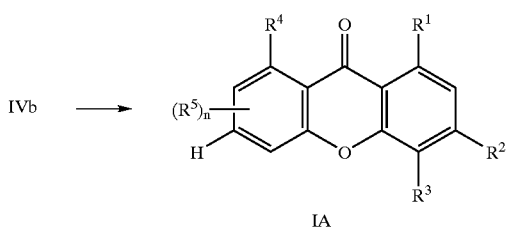

Th cyclization of IVb to compounds of the formula I in which X and Y are oxygen (formula IA) is usually carried out at temperatures of from −78° C. to 150° C., preferably from 0° C. to 50° C., in an inert organic solvent in the presence of a base [cf. Org. Prep. Proceed. Int. 10 (1978), 79].

Suitable solvents are water, aliphatic hydrocarbons, aromatic hydrocarbons, halogenated hydrocarbons, ethers, nitriles, ketones, alcohols, such as methanol, ethanol, n-propanol, isopropanol, n-butanol and tert-butanol, and also dimethyl sulfoxide, dimethylformamide and dimethyl acetamide particularly preferably $C_1$–$C_5$-alcohol/water mixtures. It is also possible to use mixtures of the solvents mentioned.

Suitable bases are, in general, inorganic compounds, such as alkali metal and alkaline earth metal hydroxides, alkali metal and alkaline earth metal oxides, alkali metal and alkaline earth metal hydrides, such as lithium hydride, sodium hydride, potassium hydride and calcium hydride, alkali metal amides, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, alkylmagnesium halides and also alkali metal and alkaline earth metal alkoxides and dimethoxymagnesium, moreover organic bases, for example tertiary amines, pyridine, substituted pyridines and also bicyclic amines. Preference is given to alkali metal hydroxides, alkali metal carbonates, alkali metal bicarbonates and alkali metal hydrides. Particular preference is given to NaOH, KOH, $NaHCO_3$ and $Na_2CO_3$.

The bases are generally employed in catalytic amounts; however, they can also be employed in equimolar amounts, in excess or, if appropriate, as solvent.

An alternative route to xanthones of the formula IA in which $R^4$ is hydroxyl, halogen, $C_1$–$C_4$-alkoxy or $C_1$–$C_4$-haloalkoxy (formula IA.1) uses alkylbenzene derivatives of the formula II.1 and 2,6-dihalogenzoyl halides of the formula III.1 as starting materials. In the formula IA.1, the variables $R^1$ to $R^3$ and $(R^5)_n$ are as defined in formula I. In the formula II.1, $R^1$, $R^2$ and $R^3$ are as defined for formula I and $R^x$ is $C_1$–$C_3$-alkoxy. In the formula III.1, Hal is halogen, such as chlorine or bromine, in particular chlorine.

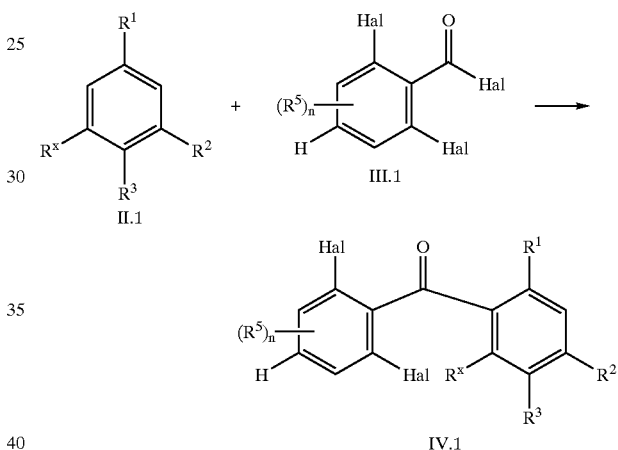

This reaction is usually carried out at temperatures of from 0° C. to 210° C., preferably from 20° C. to 50° C., in an inert organic solvent in the presence of a Lewis acid [cf. Organikum, 20th edition, Chapter 5, Joh. A. Barth Verlag, Heidelberg and Leipzig (1996)].

Suitable solvents are aliphatic hydrocarbons, aromatic hydrocarbons, such as toluene, nitrobenzene, o-, m- and p-xylene, halogenated hydrocarbons, ethers, nitriles, ketones, alcohols, such as methanol, ethanol, n-propanol, isopropanol, n-butanol and tert-butanol, and also dimethyl sulfoxide, dimethylformamide and dimethylacetamide, particularly preferably nitrobenzene or halogenated hydrocarbons, in particular methylene chloride. It is also possible to use mixtures of the solvents mentioned.

Suitable Lewis acids are, in general, main group and transition group halides, such as $BF_3$, $AlCl_3$, $FeCl_3$, $SnCl_4$, $TiCl_4$ or $ZnCl_2$.

If $R^x$ in the formula II.1 is $C_1$–$C_3$-alkoxy, the conversion to IV.1 can, by selecting a suitable Lewis acid, such as $AlCl_3$, lead directly to hydroxyl compounds IV.1 in which $R^x$ is hydroxyl.

For compounds IA.1 in which $R^4$ is not halogen, the cyclization of the compounds IV.1 is advantageously carried out with simultaneous introduction of the group $R^4$.

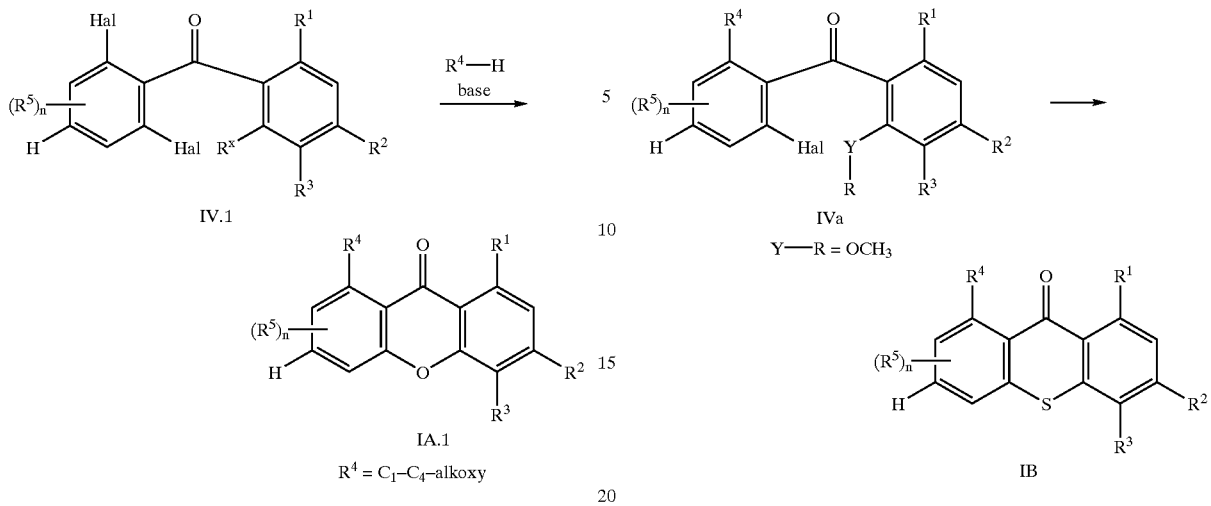

IV.1

IA.1

$R^4 = C_1–C_4$–alkoxy

IVa

Y—R = OCH₃

IB

This reaction is usually carried out at temperatures of from −78° C. to 100° C., preferably from 0° C. to 50° C., in an inert organic solvent in the presence of an alkali metal or alkaline earth metal alkoxide, which is, if appropriate, prepared in situ.

Suitable solvents are aliphatic or aromatic hydrocarbons, ethers, nitriles, ketones or alcohols, such as methanol, ethanol, n-propanol, isopropanol, n-butanol and tert-butanol, particularly preferably methanol. It is also possible to use mixtures of the solvents mentioned.

Particularly suitable for preparing the alkali metal or alkaline earth metal alkoxide are sodium or potassium.

They can be employed in equimolar amounts or in excess.

Compounds of the formula I in which $R^5$ is halogen and located in the 2-position are preferably prepared from the corresponding substituted salicylic acids of the formula III.

Compounds of the formula I in which $R^5$ is halogen and located in the 4-position are preferably prepared by halogenating xanthones I in which the position in question is unsubstituted.

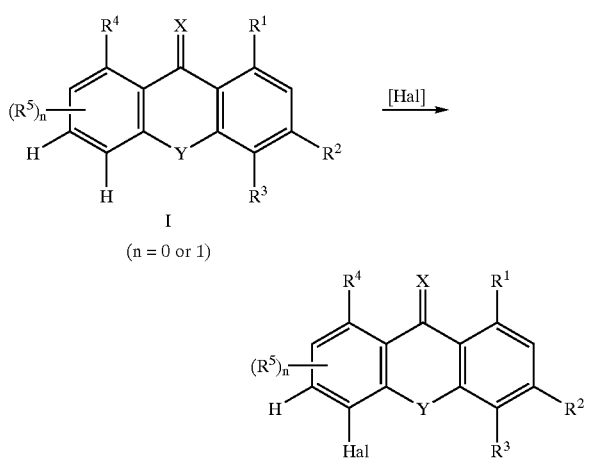

I
(n = 0 or 1)

The halogenation is carried out under conditions generally known from the literature. Suitable halogenating agents are, in particular, bromine and sulfuryl chloride.

One route to compounds of the formula IB is the sulfurization under the conditions known from GB-A 21 61 482.

A sulfurizing agent which is particularly suitable for synthesizing the compounds IB is sodium sulfide.

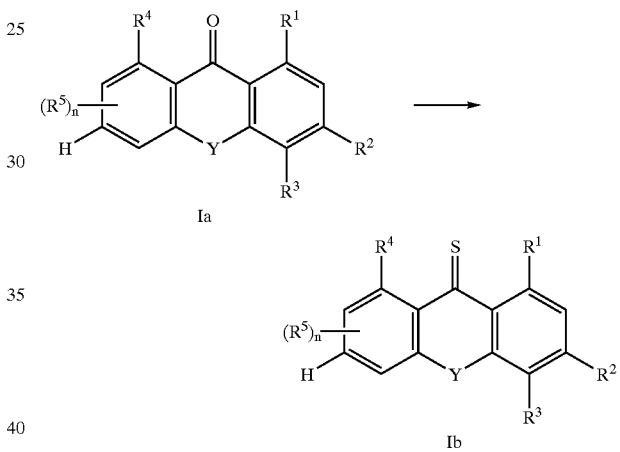

Ia

Ib

For preparing thioxanthones Ib, the sulfurization of Ia is carried out under conditions known from the literature, usually at temperatures of from 0° C. to 180° C., preferably from 20° C. to 140° C., in an inert organic solvent [cf. Liebigs Ann. Chem. (1989), 177].

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisol and tetrahydrofuran, nitriles, such as acetonitrile and propionitrile, and also dimethyl sulfoxide, particularly preferably toluene and tetrahydrofuran. It is also possible to use mixtures of the solvents mentioned.

Suitable sulfurizing agents are, for example, phosphorus pentasulfide or Lawsons reagent.

The starting materials are generally reacted with one another in equimolar amounts. In terms of yield, it may be advantageous to employ an excess of sulfurizing agent, based on Ia.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which can be purified or freed from volatile components under reduced pressure and at moderately elevated temperature. If the intermediates and end products are obtained as solids, purification can also be carried out by recrystallization or digestion.

In the definitions of the symbols given in the formulae above, collective terms were used which, in a general manner, represent the following substituents:

Halogen: fluorine, chlorine, bromine and iodine;

Alkyl: saturated, straight-chain or branched hydrocarbon radicals having 1 to 4 or 6 carbon atoms, for example $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-cahin or branched alkyl groups having 1 to 4 carbon atoms (as mentioned above), where some or all of the hydrogen atoms in these groups may be replaced by halogen atoms as mentioned above, for example $C_1$–$C_2$-haloalkyl, such as chloromethyl, bromomethyl, dichloromethyl, trichloromethyl, fluoromethyl, difluoromethyl, trifluromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 6 carbona atoms (as mentioned above) which are attached to the skeleton via an oxygen atom (—O—);

Haloalkoxy: straight-chain or branched haloalkyl groups having 1 to 6 carbon atoms (as mentioned above) which are attached to the skeleton via an oxygen atom (—O—);

alkylthio: straight-chain or branched alkyl groups having 1 to 4 carbon atoms (as mentioned above) which are attached to the skeleton via a sulfur atom (—S—);

Alkylcarbonyl: a straight-chain or branched alkyl group having 1 to 10 carbon atoms (as mentioned above) which is attached to the skeleton via a carbonyl group (—CO—);

Alkylcarbonyloxy: a straight-chain or branched alylcarbonyl group having 1 to 10 carbon atoms (as mentioned above) which is attached to the skeleton via oxygen;

Alkenyl: unsaturated, straight-chain or branched hydrocarbon radicals having 3 to 6 carbon atoms and a double bond in any position, for example $C_3$–$C_6$-alkenyl, such as 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Haloalkenyl: unsaturated, straight-chain or branched hydrocarbon radicals having 3 to 6 carbon atoms and a double bond in any position (as mentioned above), where some or all of the hydrogen atoms in these groups may be replaced by halogen atoms as mentioned above, in particular by fluorine, chlorine and bromine;

Alkenyloxy: unsaturated, straight-chain or branched hydrocarbon radicals having 3 to 6 carbon atoms and a double bond in any position which is not adjacent to the heteroatom (as mentioned above) which are attached to the skeleton via an oxygen atom (—O—);

Haloalkenyloxy: unsaturated, straight-chain or branched alkenyloxy groups having 3 to 6 carbon atoms (as mentioned above), where some or all of the hydrogen atoms in these groups may be replaced by halogen atoms as mentioned above, in particular by fluorine, chlorine and bromine;

Alkynyl: straight-chain or branched hydrocarbon groups having 3 to 6 carbon atoms and a triple bond in any position, for example $C_3$–$C_6$-alkynyl, such as 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Haloalkynyl: unsubstituted, straight-chain or branched hydrocarbon radicals having 3 to 6 carbon atoms and a triple bond in any position (as mentioned above), where some or all of the hydrogen atoms in these groups may be replaced by halogen atoms as mentioned above, in particular by fluorine, chlorine and bromine;

Alkynyloxy: unsaturated, straight-chain or branched hydrocarbon radicals having 3 to 10 carbon atoms and a triple bond in any position which is not adjacent to the heteroatom (as mentioned above), which are attached to the skeleton via an oxygen atom (—O—);

Haloalkynyloxy: unsaturated, straight-chain or branched alkynyloxy groups having 3 to 10 carbon atoms (as mentioned above), where some or all of the hydrogen atoms in these groups may be replaced by halogen atoms as mentioned above, in particular by fluorine, chlorine and bromine;

Alkylene: divalent unbranched chains of 3 to 5 $CH_2$ groups, for example $CH_2$, $CH_2CH_2$, $CH_2CH_2CH_2$, $CH_2CH_2CH_2CH_2$ and $CH_2CH_2CH_2CH_2CH_2$;

Oxyalkylene: divalent unbranched chains of 2 to 4 $CH_2$ groups, where one valency is attached to the skeleton via an oxygen atom, for example $OCH_2CH_2$, $OCH_2CH_2CH_2$ and $OCH_2CH_2CH_2CH_2$;

Oxyalkyleneoxy: divalent unbranched chains of 1 to 3 $CH_2$ groups, where both valencies are attached to the skeleton via an oxygen atom, for example $OCH_2O$, $OCH_2CH_2O$ and $OCH_2CH_2CH_2O$.

With a view to the intended use of the xanthone compounds of the formula I, particular preference is given to the following meanings of the substituents, in each case on their own or in combination;

Preference is given to compounds I in which Y is oxygen.

In addition, preference is given to compounds I in which X and Y are oxygen. They correspond to the formula I.1.

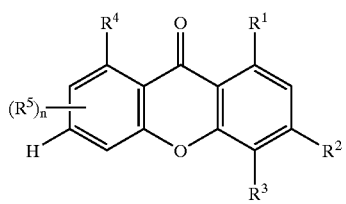

I.1

Moreover, particular preference is given to compounds I in which $R^1$ is methyl, halomethyl or ethyl, in particular methyl.

Preference is likewise given to compounds I in which $R^2$ and $R^3$ independently of one another are methoxy, ethoxy or n-butoxy, in particular methoxy or n-butoxy, with particular preference methoxy.

Moreover, preference is given to compounds I in which one of the radicals $R^2$ and $R^3$ is methoxy.

Particular preference is given to compounds I in which $R^1$ is methyl and $R^2$ and $R^3$ are methoxy.

Particular preference is furthermore given to compounds I in which $R^4$ is halogen, cyano, hydroxyl, methyl, methoxy, alkylcarbonyloxy, halomethyl or halomethoxy.

In addition, particular preference is given to compounds I in which $R^4$ is fluorine, chlorine, bromine, iodine, hydroxyl, amino, methyl, $C_1$–$C_4$-haloalkyl, methoxy, $C_1$–$C_4$-haloalkoxy or $C_1$–$C_4$-alkylthio.

Particular preference is likewise given to compounds I in which $R^4$ is hydroxyl, amino, methyl, $C_1$-haloalkyl, methoxy, $C_1$-haloalkoxy or $C_1$-alkylthio.

Preference is given to compounds I in which $R^4$ is $OCH_mF_{3-m}$, where m is an integer from 0 to 3, in particular $OCF_3$ or $OCHF_2$.

In addition, particular preference is given to compounds I in which $R^5$ is halogen, in particular chlorine or bromine.

Particular preference is also given to compounds I in which n is 1.

Furthermore, preference is given to compounds I in which $R^4$ is $OCH_mF_{3-m}$, and $R^5$ is halogen or $OCF_mF_{3-m}$, where m is an integer from 0 to 2.

Moreover, preference is given to compounds I in which $R^1$ is $C_1$–$C_4$-alkyl or $CF_3$, $R^2$ and $R^3$ are in each case identical or different and are $C_1$–$C_4$-alkoxy, $R^4$ is halogen, $C_1$–$C_4$-alkyl, $CF_3$, $CHF_2$, hydroxyl, $C_1$–$C_4$-alkoxy, $OCHF_2$, $C_1$–$C_4$-alkoxycarbonyl, mercapto or amino and $(R^5)_n$ is hydrogen, halogen, methyl, hydroxyl, $CF_3$ or $OCHF_2$.

In particular with a view to their use, preference is given to the compounds I compiled in the tables below. Moreover, the groups mentioned in the tables for a substituent are on their own, independently of the combination in which they are mentioned, a particularly preferred embodiment of the substituent in question.

TABLE 1

Compounds of the formula I.1 is which $R^1$ is methyl, $R^2$ and $R^3$ are methoxy and the combination of the radicals $R^4$ and $(R^5)_n$ for a compound corresponds in each case to one row of Table A

TABLE 2

Compounds of the formula I.1 is which $R^1$ is methyl, $R^2$ is methoxy and $R^3$ is ethoxy and the combination of the radicals $R^4$ and $(R^5)_n$ for a compound corresponds in each case to one row of Table A

TABLE 3

Compounds of the formula I.1 is which $R^1$ is methyl, $R^2$ is methoxy and $R^3$ are n-propoxy and the combination of the radicals $R^{4\ and\ (R5)}{}_n$ for a compound corresponds in each case to one row of Table A

TABLE 4

Compounds of the formula I.1 is which $R^1$ is methyl, $R^2$ is methoxy and $R^3$ are isopropoxy and the combination of the radicals $R^{4\ and\ (R5)}{}_n$ for a compound corresponds in each case to one row of Table A

TABLE 5

Compounds of the formula I.1 is which $R^1$ is methyl, $R^2$ is methoxy and $R^3$ is n-butoxy and the combination of the radicals $R^4$ and $(R^5)_n$ for a compound corresponds in each case to one row of Table A

TABLE 6

Compounds of the formula I.1 is which $R^1$ is methyl, $R^2$ is ethoxy and $R^3$ are methoxy and the combination of the radicals $R^4$ and $(R^5)_n$ for a compound corresponds in each case to one row of Table A

TABLE 7

Compounds of the formula I.1 is which $R^1$ is methyl, $R^2$ is n-propoxy and $R^3$ are methoxy and the combination of the radicals $R^{4\ and\ (R5)}{}_n$ for a compound corresponds in each case to one row of Table A

TABLE 8

Compounds of the formula I.1 is which $R^1$ is methyl, $R^2$ is isopropoxy and $R^3$ is methoxy and the combination of the radicals $R^4$ and $(R^5)_n$ for a compound corresponds in each case to one row of Table A

TABLE 9

Compounds of the formula I.1 is which $R^1$ is methyl, $R^2$ is n-butoxy and $R^3$ are methoxy and the combination of the radicals $R^{4\ and\ (R5)}{}_n$ for a compound corresponds in each case to one row of Table A

TABLE 10

Compounds of the formula I.1 is which $R^1$ is chloromethyl, $R^2$ and $R^3$ are methoxy and the combination of the radicals $R^4$ and $(R^5)_n$ for a compound corresponds in each case to one row of Table A

TABLE 11

Compounds of the formula I.1 is which $R^1$ is chloromethyl, $R^2$ is methoxy and $R^3$ are ethoxy and the combination of the radicals $R^4$ and $(R^5)_n$ for a compound corresponds in each case to one row of Table A

TABLE 12

Compounds of the formula I.1 is which $R^1$ is chloromethyl, $R^2$ is methoxy and $R^3$ are n-propoxy and the combination of the radicals $R^4$ and $(R^5)_n$ for a compound corresponds in each case to one row of Table A

TABLE 13

Compounds of the formula I.1 in which $R^1$ is chloromethyl, $R^2$ is methoxy and $R^3$ is isopropoxy and the combination of the radicals $R^4$ and $(R^5)_n$ for a compound corresponds in each case to one row of Table A

TABLE 14

Compounds of the formula I.1 in which $R^1$ is chloromethyl, $R^2$ is methoxy and $R^3$ is n-butoxy and the combination of the radicals $R^4$ and $(R^5)_n$ for a compound corresponds in each case to one row of Table A

TABLE 15

Compounds of the formula I.1 in which $R^1$ is chloromethyl, $R^2$ is ethoxy and $R^3$ is methoxy and the combination of the radicals $R^4$ and $(R^5)_n$ for a compound corresponds in each case to one row of Table A

TABLE 16

Compounds of the formula I.1 in which $R^1$ is chloromethyl, $R^2$ and $R^3$ is ethoxy and the combination of the radicals $R^4$ and $(R^5)_n$ for a compound corresponds in each case to one row of Table A

TABLE 17

Compounds of the formula I.1 in which $R^1$ is chloromethyl, $R^2$ is n-propoxy and $R^3$ is methoxy and the combination of the radicals $R^4$ and $(R^5)_n$ for a compound corresponds in each case to one row of Table A

TABLE 18

Compounds of the formula I.1 in which $R^1$ is chloromethyl, $R^2$ is isopropoxy and $R^3$ is methoxy and the combination of the radicals $R^4$ and $(R^5)_n$ for a compound corresponds in each case to one row of Table A

TABLE 19

Compounds of the formula I.1 in which $R^1$ is chloromethyl, $R^2$ is n-butoxy and $R^3$ is methoxy and the combination of the radicals $R^4$ and $(R^5)_n$ for a compound corresponds in each case to one row of Table A

TABLE 20

Compounds of the formula I.1 in which $R^1$ is fluoromethyl, $R^2$ and $R^3$ is methoxy and the combination of the radicals $R^4$ and $(R^5)_n$ for a compound corresponds in each case to one row of Table A

TABLE 21

Compounds of the formula I.1 in which $R^1$ is fluoromethyl, $R^2$ is methoxy and $R^3$ is ethoxy and the combination of the radicals $R^4$ and $(R^5)_n$ for a compound corresponds in each case to one row of Table A

TABLE 22

Compounds of the formula I.1 in which $R^1$ is fluoromethyl, $R^2$ is methoxy and $R^3$ is n-propoxy and the combination of the radicals $R^4$ and $(R^5)_n$ for a compound corresponds in each case to one row of Table A

TABLE 23

Compounds of the formula I.1 in which $R^1$ is fluoromethyl, $R^2$ is methoxy and $R^3$ is isopropoxy and the combination of the radicals $R^4$ and $(R^5)_n$ for a compound corresponds in each case to one row of Table A

TABLE 24

Compounds of the formula I.1 in which $R^1$ is fluoromethyl, $R^2$ is methoxy and $R^3$ is n-butoxy and the combination of the radicals $R^4$ and $(R^5)_n$ for a compound corresponds in each case to one row of Table A

TABLE 25

Compounds of the formula I.1 in which $R^1$ is fluoromethyl, $R^2$ is ethoxy and $R^3$ is methoxy and the combination of the radicals $R^4$ and $(R^5)_n$ for a compound corresponds in each case to one row of Table A

TABLE 26

Compounds of the formula I.1 in which $R^1$ is fluoromethyl, $R^2$ is n-propoxy and $R^3$ is methoxy and the combination of the radicals $R^4$ and $(R^5)_n$ for a compound corresponds in each case to one row of Table A

TABLE 27

Compounds of the formula I.1 in which $R^1$ is fluoromethyl, $R^2$ is isopropoxy and $R^3$ is methoxy and the combination of the radicals $R^4$ and $(R^5)_n$ for a compound corresponds in each case to one row of Table A

TABLE 28

Compounds of the formula I.1 in which $R^1$ is fluoromethyl, $R^2$ is n-butoxy and $R^3$ is methoxy and the combination of the radicals $R^4$ and $(R^5)_n$ for a compound corresponds in each case to one row of Table A

TABLE A

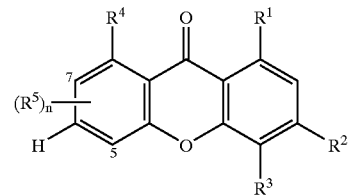

I.1

| No. | $R^4$ | $(R^5)_n$ |
|---|---|---|
| A-1 | $CH_3$ | 7-Cl |
| A-2 | $CH_2CH_3$ | 7-Cl |
| A-3 | $CH_2CH_2CH_3$ | 7-Cl |
| A-4 | $CH(CH_3)_2$ | 7-Cl |
| A-5 | $CH_2Cl$ | 7-Cl |
| A-6 | $CH_2F$ | 7-Cl |
| A-7 | $CHCl_2$ | 7-Cl |
| A-8 | $CHF_2$ | 7-Cl |
| A-9 | $CCl_3$ | 7-Cl |
| A-10 | $CF_3$ | 7-Cl |
| A-11 | F | 7-Cl |
| A-12 | Cl | 7-Cl |
| A-13 | Br | 7-Cl |
| A-14 | OH | 7-Cl |
| A-15 | SH | 7-Cl |
| A-16 | $OCH_3$ | 7-Cl |
| A-17 | $OCH_2CH_3$ | 7-Cl |
| A-18 | $OCH_2CH_2CH_3$ | 7-Cl |
| A-19 | $OCH(CH_3)_2$ | 7-Cl |
| A-20 | $OCH_2Cl$ | 7-Cl |
| A-21 | $OCH_2F$ | 7-Cl |
| A-22 | $OCHCl_2$ | 7-Cl |
| A-23 | $OCHF_2$ | 7-Cl |
| A-24 | $OCCl_3$ | 7-Cl |
| A-25 | $OCF_3$ | 7-Cl |
| A-26 | $NH_2$ | 7-Cl |
| A-27 | $OC(=O)CH_3$ | 7-Cl |
| A-28 | $OC(=O)CH_2CH_3$ | 7-Cl |
| A-29 | $OC(=O)CH(CH_3)_2$ | 7-Cl |
| A-30 | $OC(=O)CH_2CH_2CH_3$ | 7-Cl |
| A-31 | $OC(=O)CH(CH_3)CH_2Cl$ | 7-Cl |
| A-32 | $OC(=O)CH(CH_3)CH_2Br$ | 7-Cl |
| A-33 | $CH_3$ | 7-Br |
| A-34 | $CH_2CH_3$ | 7-Br |
| A-35 | $CH_2CH_2CH_3$ | 7-Br |
| A-36 | $CH(CH_3)_2$ | 7-Br |
| A-37 | $CH_2Cl$ | 7-Br |
| A-38 | $CH_2F$ | 7-Br |
| A-39 | $CHCl_2$ | 7-Br |
| A-40 | $CHF_2$ | 7-Br |
| A-41 | $CCl_3$ | 7-Br |
| A-42 | $CF_3$ | 7-Br |
| A-43 | F | 7-Br |
| A-44 | Cl | 7-Br |
| A-45 | Br | 7-Br |
| A-46 | OH | 7-Br |
| A-47 | SH | 7-Br |
| A-48 | $OCH_3$ | 7-Br |
| A-49 | $OCH_2CH_3$ | 7-Br |
| A-50 | $OCH_2CH_2CH_3$ | 7-Br |
| A-51 | $OCH(CH_3)_2$ | 7-Br |
| A-52 | $OCH_2Cl$ | 7-Br |
| A-53 | $OCH_2F$ | 7-Br |
| A-54 | $OCHCl_2$ | 7-Br |
| A-55 | $OCHF_2$ | 7-Br |
| A-56 | $OCCl_3$ | 7-Br |
| A-57 | $OCF_3$ | 7-Br |
| A-58 | $NH_2$ | 7-Br |
| A-59 | $OC(=O)CH_3$ | 7-Br |
| A-60 | $OC(=O)CH_2CH_3$ | 7-Br |
| A-61 | $OC(=O)CH(CH_3)_2$ | 7-Br |
| A-62 | $OC(=O)CH_2CH_2CH_3$ | 7-Br |
| A-63 | $OC(=O)CH(CH_3)CH_2Cl$ | 7-Br |
| A-64 | $OC(=O)CH(CH_3)CH_2Br$ | 7-Br |
| A-65 | $CH_3$ | 5-Cl |
| A-66 | $CH_2CH_3$ | 5-Cl |
| A-67 | $CH_2CH_2CH_3$ | 5-Cl |
| A-68 | $CH(CH_3)_2$ | 5-Cl |
| A-69 | $CH_2Cl$ | 5-Cl |
| A-70 | $CH_2F$ | 5-Cl |
| A-71 | $CHCl_2$ | 5-Cl |
| A-72 | $CHF_2$ | 5-Cl |
| A-73 | $CCl_3$ | 5-Cl |
| A-74 | $CF_3$ | 5-Cl |
| A-75 | F | 5-Cl |
| A-76 | Cl | 5-Cl |
| A-77 | Br | 5-Cl |
| A-78 | OH | 5-Cl |
| A-79 | SH | 5-Cl |
| A-80 | $OCH_3$ | 5-Cl |
| A-81 | $OCH_2CH_3$ | 5-Cl |
| A-82 | $OCH_2CH_2CH_3$ | 5-Cl |
| A-83 | $OCH(CH_3)_2$ | 5-Cl |
| A-84 | $OCH_2Cl$ | 5-Cl |
| A-85 | $OCH_2F$ | 5-Cl |
| A-86 | $OCHCl_2$ | 5-Cl |
| A-87 | $OCHF_2$ | 5-Cl |
| A-88 | $OCCl_3$ | 5-Cl |
| A-89 | $OCF_3$ | 5-Cl |
| A-90 | $NH_2$ | 5-Cl |
| A-91 | $OC(=O)CH_3$ | 5-Cl |
| A-92 | $OC(=O)CH_2CH_3$ | 5-Cl |
| A-93 | $OC(=O)CH(CH_3)_2$ | 5-Cl |
| A-94 | $OC(=O)CH_2CH_2CH_3$ | 5-Cl |
| A-95 | $OC(=O)CH(CH_3)CH_2Cl$ | 5-Cl |
| A-96 | $OC(=O)CH(CH_3)CH_2Br$ | 5-Cl |
| A-97 | $CH_3$ | 5-Br |
| A-98 | $CH_2CH_3$ | 5-Br |
| A-99 | $CH_2CH_2CH_3$ | 5-Br |
| A-100 | $CH(CH_3)_2$ | 5-Br |
| A-101 | $CH_2Cl$ | 5-Br |
| A-102 | $CH_2F$ | 5-Br |
| A-103 | $CHCl_2$ | 5-Br |
| A-104 | $CHF_2$ | 5-Br |
| A-105 | $CCl_3$ | 5-Br |
| A-106 | $CF_3$ | 5-Br |
| A-107 | F | 5-Br |
| A-108 | Cl | 5-Br |
| A-109 | Br | 5-Br |
| A-110 | OH | 5-Br |
| A-111 | SH | 5-Br |
| A-112 | $OCH_3$ | 5-Br |
| A-113 | $OCH_2CH_3$ | 5-Br |
| A-114 | $OCH_2CH_2CH_3$ | 5-Br |
| A-115 | $OCH(CH_3)_2$ | 5-Br |
| A-116 | $OCH_2Cl$ | 5-Br |
| A-117 | $OCH_2F$ | 5-Br |
| A-118 | $OCHCl_2$ | 5-Br |
| A-119 | $OCHF_2$ | 5-Br |
| A-120 | $OCCl_3$ | 5-Br |
| A-121 | $OCF_3$ | 5-Br |

TABLE A-continued

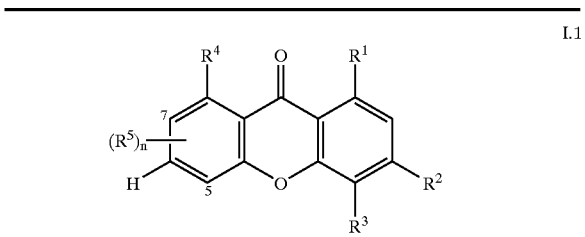

| No. | R⁴ | (R⁵)ₙ |
|---|---|---|
| A-122 | NH₂ | 5-Br |
| A-123 | OC(=O)CH₃ | 5-Br |
| A-124 | OC(=O)CH₂CH₃ | 5-Br |
| A-125 | OC(=O)CH(CH₃)₂ | 5-Br |
| A-126 | OC(=O)CH₂CH₂CH₃ | 5-Br |
| A-127 | OC(=O)CH(CH₃)CH₂Cl | 5-Br |
| A-128 | OC(=O)CH(CH₃)CH₂Br | 5-Br |
| A-129 | CH₃ | 5,7-Cl₂ |
| A-130 | CH₂CH₃ | 5,7-Cl₂ |
| A-131 | CH₂CH₂CH₃ | 5,7-Cl₂ |
| A-132 | CH(CH₃)₂ | 5,7-Cl₂ |
| A-133 | CH₂Cl | 5,7-Cl₂ |
| A-134 | CH₂F | 5,7-Cl₂ |
| A-135 | CHCl₂ | 5,7-Cl₂ |
| A-136 | CHF₂ | 5,7-Cl₂ |
| A-137 | CCl₃ | 5,7-Cl₂ |
| A-138 | CF₃ | 5,7-Cl₂ |
| A-139 | F | 5,7-Cl₂ |
| A-140 | Cl | 5,7-Cl₂ |
| A-141 | Br | 5,7-Cl₂ |
| A-142 | OH | 5,7-Cl₂ |
| A-143 | SH | 5,7-Cl₂ |
| A-144 | OCH₃ | 5,7-Cl₂ |
| A-145 | OCH₂CH₃ | 5,7-Cl₂ |
| A-146 | OCH₂CH₂CH₃ | 5,7-Cl₂ |
| A-147 | OCH(CH₃)₂ | 5,7-Cl₂ |
| A-148 | OCH₂Cl | 5,7-Cl₂ |
| A-149 | OCH₂F | 5,7-Cl₂ |
| A-150 | OCHCl₂ | 5,7-Cl₂ |
| A-151 | OCHF₂ | 5,7-Cl₂ |
| A-152 | OCCl₃ | 5,7-Cl₂ |
| A-153 | OCF₃ | 5,7-Cl₂ |
| A-154 | NH₂ | 5,7-Cl₂ |
| A-155 | OC(=O)CH₃ | 5,7-Cl₂ |
| A-156 | OC(=O)CH₂CH₃ | 5,7-Cl₂ |
| A-157 | OC(=O)CH(CH₃)₂ | 5,7-Cl₂ |
| A-158 | OC(=O)CH₂CH₂CH₃ | 5,7-Cl₂ |
| A-159 | OC(=O)CH(CH₃)CH₂Cl | 5,7-Cl₂ |
| A-160 | OC(=O)CH(CH₃)CH₂Br | 5,7-Cl₂ |
| A-161 | CH₃ | 5,7-Br₂ |
| A-162 | CH₂CH₃ | 5,7-Br₂ |
| A-163 | CH₂CH₂CH₃ | 5,7-Br₂ |
| A-164 | CH(CH₃)₂ | 5,7-Br₂ |
| A-165 | CH₂Cl | 5,7-Br₂ |
| A-166 | CH₂F | 5,7-Br₂ |
| A-167 | CHCl₂ | 5,7-Br₂ |
| A-168 | CHF₂ | 5,7-Br₂ |
| A-169 | CCl₃ | 5,7-Br₂ |
| A-170 | CF₃ | 5,7-Br₂ |
| A-171 | F | 5,7-Br₂ |
| A-172 | Cl | 5,7-Br₂ |
| A-173 | Br | 5,7-Br₂ |
| A-174 | OH | 5,7-Br₂ |
| A-175 | SH | 5,7-Br₂ |
| A-176 | OCH₃ | 5,7-Br₂ |
| A-177 | OCH₂CH₃ | 5,7-Br₂ |
| A-178 | OCH₂CH₂CH₃ | 5,7-Br₂ |
| A-179 | OCH(CH₃)₂ | 5,7-Br₂ |
| A-180 | OCH₂Cl | 5,7-Br₂ |
| A-181 | OCH₂F | 5,7-Br₂ |
| A-182 | OCHCl₂ | 5,7-Br₂ |
| A-183 | OCHF₂ | 5,7-Br₂ |
| A-184 | OCCl₃ | 5,7-Br₂ |
| A-185 | OCF₃ | 5,7-Br₂ |
| A-186 | NH₂ | 5,7-Br₂ |
| A-187 | OC(=O)CH₃ | 5,7-Br₂ |
| A-188 | OC(=O)CH₂CH₃ | 5,7-Br₂ |
| A-189 | OC(=O)CH(CH₃)₂ | 5,7-Br₂ |
| A-190 | OC(=O)CH₂CH₂CH₃ | 5,7-Br₂ |
| A-191 | OC(=O)CH(CH₃)CH₂Cl | 5,7-Br₂ |
| A-192 | OC(=O)CH(CH₃)CH₂Br | 5,7-Br₂ |
| A-193 | CH₃ | 7-CH₃ |
| A-194 | CH₂CH₃ | 7-CH₃ |
| A-195 | CH₂CH₂CH₃ | 7-CH₃ |
| A-196 | CH(CH₃)₂ | 7-CH₃ |
| A-197 | CH₂Cl | 7-CH₃ |
| A-198 | CH₂F | 7-CH₃ |
| A-199 | CHCl₂ | 7-CH₃ |
| A-200 | CHF₂ | 7-CH₃ |
| A-201 | CCl₃ | 7-CH₃ |
| A-202 | CF₃ | 7-CH₃ |
| A-203 | F | 7-CH₃ |
| A-204 | Cl | 7-CH₃ |
| A-205 | Br | 7-CH₃ |
| A-206 | OH | 7-CH₃ |
| A-207 | SH | 7-CH₃ |
| A-208 | OCH₃ | 7-CH₃ |
| A-209 | OCH₂CH₃ | 7-CH₃ |
| A-210 | OCH₂CH₂CH₃ | 7-CH₃ |
| A-211 | OCH(CH₃)₂ | 7-CH₃ |
| A-212 | OCH₂Cl | 7-CH₃ |
| A-213 | OCH₂F | 7-CH₃ |
| A-214 | OCHCl₂ | 7-CH₃ |
| A-215 | OCHF₂ | 7-CH₃ |
| A-216 | OCCl₃ | 7-CH₃ |
| A-217 | OCF₃ | 7-CH₃ |
| A-218 | NH₂ | 7-CH₃ |
| A-219 | OC(=O)CH₃ | 7-CH₃ |
| A-220 | OC(=O)CH₂CH₃ | 7-CH₃ |
| A-221 | OC(=O)CH(CH₃)₂ | 7-CH₃ |
| A-222 | OC(=O)CH₂CH₂CH₃ | 7-CH₃ |
| A-223 | OC(=O)CH(CH₃)CH₂Cl | 7-CH₃ |
| A-224 | OC(=O)CH(CH₃)CH₂Br | 7-CH₃ |
| A-225 | CH₃ | 5-CH₃ |
| A-226 | CH₂CH₃ | 5-CH₃ |
| A-227 | CH₂CH₂CH₃ | 5-CH₃ |
| A-228 | CH(CH₃)₂ | 5-CH₃ |
| A-229 | CH₂Cl | 5-CH₃ |
| A-230 | CH₂F | 5-CH₃ |
| A-231 | CHCl₂ | 5-CH₃ |
| A-232 | CHF₂ | 5-CH₃ |
| A-233 | CCl₃ | 5-CH₃ |
| A-234 | CF₃ | 5-CH₃ |
| A-235 | F | 5-CH₃ |
| A-236 | Cl | 5-CH₃ |
| A-237 | Br | 5-CH₃ |
| A-238 | OH | 5-CH₃ |
| A-239 | SH | 5-CH₃ |
| A-240 | OCH₃ | 5-CH₃ |
| A-241 | OCH₂CH₃ | 5-CH₃ |
| A-242 | OCH₂CH₂CH₃ | 5-CH₃ |
| A-243 | OCH(CH₃)₂ | 5-CH₃ |
| A-244 | OCH₂Cl | 5-CH₃ |
| A-245 | OCH₂F | 5-CH₃ |
| A-246 | OCHCl₂ | 5-CH₃ |
| A-247 | OCHF₂ | 5-CH₃ |
| A-248 | OCCl₃ | 5-CH₃ |
| A-249 | OCF₃ | 5-CH₃ |
| A-250 | NH₂ | 5-CH₃ |
| A-251 | OC(=O)CH₃ | 5-CH₃ |

TABLE A-continued

L.1

$$\text{(structure: xanthone core with } R^4 \text{ at 8, } R^1 \text{ at 1, } R^2 \text{ at 4, } R^3 \text{ at 3, } (R^5)_n \text{ at position 7, H at 5)}$$

| No. | R⁴ | (R⁵)ₙ |
|---|---|---|
| A-252 | OC(=O)CH₂CH₃ | 5-CH₃ |
| A-253 | OC(=O)CH(CH₃)₂ | 5-CH₃ |
| A-254 | OC(=O)CH₂CH₂CH₃ | 5-CH₃ |
| A-255 | OC(=O)CH(CH₃)CH₂Cl | 5-CH₃ |
| A-256 | OC(=O)CH(CH₃)CH₂Br | 5-CH₃ |
| A-257 | CH₃ | 5,7-(CH₃)₂ |
| A-258 | CH₂CH₃ | 5,7-(CH₃)₂ |
| A-259 | CH₂CH₂CH₃ | 5,7-(CH₃)₂ |
| A-260 | CH(CH₃)₂ | 5,7-(CH₃)₂ |
| A-261 | CH₂Cl | 5,7-(CH₃)₂ |
| A-262 | CH₂F | 5,7-(CH₃)₂ |
| A-263 | CHCl₂ | 5,7-(CH₃)₂ |
| A-264 | CHF₂ | 5,7-(CH₃)₂ |
| A-265 | CCl₃ | 5,7-(CH₃)₂ |
| A-266 | CF₃ | 5,7-(CH₃)₂ |
| A-267 | F | 5,7-(CH₃)₂ |
| A-268 | Cl | 5,7-(CH₃)₂ |
| A-269 | Br | 5,7-(CH₃)₂ |
| A-270 | OH | 5,7-(CH₃)₂ |
| A-271 | SH | 5,7-(CH₃)₂ |
| A-272 | OCH₃ | 5,7-(CH₃)₂ |
| A-273 | OCH₂CH₃ | 5,7-(CH₃)₂ |
| A-274 | OCH₂CH₂CH₃ | 5,7-(CH₃)₂ |
| A-275 | OCH(CH₃)₂ | 5,7-(CH₃)₂ |
| A-276 | OCH₂Cl | 5,7-(CH₃)₂ |
| A-277 | OCH₂F | 5,7-(CH₃)₂ |
| A-278 | OCHCl₂ | 5,7-(CH₃)₂ |
| A-279 | OCHF₂ | 5,7-(CH₃)₂ |
| A-280 | OCCl₃ | 5,7-(CH₃)₂ |
| A-281 | OCF₃ | 5,7-(CH₃)₂ |
| A-282 | NH₂ | 5,7-(CH₃)₂ |
| A-283 | OC(=O)CH₃ | 5,7-(CH₃)₂ |
| A-284 | OC(=O)CH₂CH₃ | 5,7-(CH₃)₂ |
| A-285 | OC(=O)CH(CH₃)₃ | 5,7-(CH₃)₂ |
| A-286 | OC(=O)CH₂CH₂CH₃ | 5,7-(CH₃)₂ |
| A-287 | OC(=O)CH(CH₃)CH₂Cl | 5,7-(CH₃)₂ |
| A-288 | OC(=O)CH(CH₃)CH₂Br | 5,7-(CH₃)₂ |

The compounds I are suitable for use as fungicides. They have excellent activity against a broad spectrum of phytopathogenic fungi, in particular from the class of the Ascomycetes, Deuteromycetes, Phycomycetes and Basidiomycetes. Some of them have systemic activity and can be used in crop protection as foliar and soil fungicides.

They are especially important for controlling a large number of fungi in a variety of crop plants such as wheat, rye, barley, oats, rice, maize, grass, bananas, cotton, soybean, coffee, sugar cane, grapevines, fruit species, ornamentals and vegetable species such as cucumbers, beans, tomatoes, potatoes and cucurbits, and also in the seeds of these plants.

Specifically, they are suitable for controlling the following plant diseases:

Alternate species, Podosphaera species, Sclerotinia species, Physalospora canker in vegetables and fruit.

Botrytis cinerea (gray mold) in strawberries, vegetables, ornamentals and grapevines, Corynespora cassiicola in cucumbers, Colletotrichum species in fruit and vegetables, Diplocarpon rosae in roses.

Elsinoe fawcetti and Diaporthe citri in citrus fruits,

Sphaerotheca species in cucurbits, strawberries and roses,

Cercospora species in groundnuts, sugar beet and eggplants,

Erysiphe cichoracearum in cucurbits,

Leveillula taurica in bell peppers, tomatoes and eggplants,

Mycosphaerella species in applies and Japanese apricot,

Phyllactinia kakicola, Gloesporium kaki, in Japanese apricot,

Gymnosporangium yamadae, Leptothyrium pomi, Podosphaera leucotricha and Gloedes pomigena in apples, Cladosporium carpophilum in pears and Japanese apricot, Phomopsis species in pears, Phytophthora species in citrus fruits, potatoes, onions, in particular Phytophthora infestans in potatoes and tomatoes, Blumeria graminis (powdery mildew) in cereals, Fusarium and Verticillium species in a variety of platns, Glomerella cingulata in tea, Drechslera and Bipolaris species in cereals and rice, Mycosphaerella species in bananas and groundnuts, Plasmopara viticola in grapevines, Personospora species in onions, spinach and chrysanthemums, Phaeoisariposis vitis and Sphaceloma ampelina in grapefruits, Pseudocercosporella herpotrichoides in wheat and barley, Pseudoperonospora species in hops and cucumbers, Puccinia species and Typhula species in cereals and lawn, Pyricularia oryzae in rice, Rhizoctonia species in cotton, rice and lawn, Stagonospora nodorum and Septoria tritici in wheat, Uncinula necator in grapevines, Ustilago species in cereals and sugar cane, and also Venturia species (scab) in applies and pears.

The compounds I are also suitable for controlling harmful fungi such as Paecilomyces variotii in the protection of materials (for example wood, paper, paint dispersions, fibers or tissues) and in the protection of stored products.

The compounds I are employed by treating the fungi or the plants, seeds, materials or the soil to be protected against fungal attack with a fungicidally effective amount of the active compounds. The application can be carried out before or after the infection of the materials, plants or seeds by the fungi.

The fungicidal compositions generally comprise from 0.1 to 95, preferably from 0.5 to 90,% by weight of active compound.

For use in crop protection, the application rates are, depending on the kind of effect desired, from 0.01 to 2.0 kg of active compound per ha.

The treatment of seeds generally requires active compound quantities of from 0.001 to 0.1 g, preferably from 0.01 to 0.05 g, per kilogram of seed.

For use in the protection of materials or stored products, the active compound application rate depends on the kind of application area and effect desired. Customary application rates in the protection of materials are, for example, from 0.001 g to 2 kg, preferably from 0.005 g to 1 kg, of active compound per cubic meter of treated material.

The compounds I can be converted into the customary formulations, e.g. solutions, emulsions, suspensions, dusts, powders, pastes and granules. The use form depends on the specific intended use; in any case, it should ensure fine and uniform distribution of the compound according to the invention.

The formulations are prepared in a known manner, e.g. by extending the active compound with solvents and/or carriers, if desired using emulsifiers and dispersants, it being possible to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic mienrals (e.g. finely divided silica, silicates); emulsifiers such as nonionic and anionic emulsifiers (e.g. polyoxyethylene fatty alcohol ethers, alkylsulfonates and arylsulfonates), and dispersants such as lignosulfite waste liquors and methylcellulose.

Suitable surfactants are the alkali metal, alkaline earth metal and ammonium salts of lignosulfonic acid, naphthalenesulfonic acid, phenolsulfonic acid, and dibutylnaphthalenesulfonic acid, alkylarylsulfonates, alkyl sulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalene sulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for preparing directly sprayable solutions, emulsions, pastes or oil dispersions are petroleum fractions having medium to high boiling points, such as kerosene or diesel oil, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone, and water.

Powders, compositions for broadcasting and dusts can be prepared by mixing or jointly grinding the active substances with a solid carrier.

Granules, for example coated granules, impregnated granules and homogenous granules, can be prepared by binding the active compounds to solid carriers. Solid carriers are, for example, mineral earths, such as silica gel, silicas, silicates, talc, kaolin, atta clay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to the NMR spectrum).

Examples of formulations are:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 ml of ethylene oxide to 1 mol of castor oil (active compound content 16% by weight).

V. 80 parts by weight of a compound according to the invention are mixed well with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel, and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound content 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100 000 parts by weight of water and finely dispersed therein, affording an aqueous dispersion comprising 0.02% by weight of active compound.

VIII. 20 parts by weight of a compound according to the invention are mixed well with 3 parts by weight of the sodium salt of diisobutylnaphthalene-α-sulfonic acid, 17 parts of weight of the sodium salt of a lignosulfonic acid from a sulfite waste liquor and 60 parts by weight of pulverulent silica gel, and ground in a hammer mill. The mixture is finely dispersed in 20 000 parts by weight, affording a spray liquor comprising 0.1% by weight of active compound.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting, or granules, by spraying, atomizing, dusting, broadcasting or watering. The application forms depend entirely on the intended uses; in any case, they should ensure very fine dispersion of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active compound, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%, preferably from 0.01 to 1%.

It is also possible to use the active compounds with a high degree of success in the ultra-low-volume (ULV) method, it being possible to apply formulations comprising more than 95% by weight of active compound or even the active compound without additives.

Oils of various types, herbicides, fungicides, other pesticides and bactericides can be added to the active compounds, if desired even immediately prior to application (tank mix). These agents can be added to the compositions according to the invention in a weight ratio of 1:10 to 10:1.

The compositions according to the invention in the use form as fungicides may also be present in combination with other active compounds, for example with herbicides, insecticides, growth regulators, fungicides or else with fertilizers. In many cases, a mixture of the compounds I, or of the compositions comprising them, in the use form as fungicides with other fungicides results in a broader fungicidal spectrum of activity.

The following list of fungicides in combination with which the compounds according to the invention can be used is intended to illustrate the possible combinations, but not to impose any limitations:

- sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;
- nitro derivatives, such as dinitro-(1-methylheptyl)phenyl crotonate, 7-sec-butyl-4,6-dinitrophenyl-3,3-dimethyl acrylate, 2-sec-butyl-4,6-dinitrophenylisopropyl carbonate, diisopropyl 5-nitroisophthalate;
- heterocyclic substances, such as 2-heptadecyl-2-imidazoline acetate, 2-chloro-N-(4'-chlorobiphenyl-2-yl)nicotinamide, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl)-((2))benzimidazole, 2-(thiazolyl-(4))-benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-1-(2,2,2-trichloroethyl) formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis-(3-methoxycarbonyl-2-thioureido)benzene,
- strobilurins, such as methyl E-methoximino-[α-(o-tolyloxy)-o-tolyl]acetate, methyl E-2-{2-[6-(2-cyanophenoxy)pyrimidin-4-yloxy]phenyl}-3-methoxyacrylate, methyl-E-methoxyimino-[α-(2-phenoxyphenyl)]acetamide, methyl-E-methoxyimino-[α-(2,5-dimethylphenoxy)-o-tolyl]acetamide, methyl E-2-(2-[2-trifluoromethylpyrid-6-yl]oxymethyl] phenyl}-3-methoxy acrylate, methyl (E,E)-methoximino-(2-[1-(3-trifluoromethylphenyl) ethylideneaminooxymethyl]phenyl}acetate, methyl N-(2-{(1-(4-chlorophenyl)-1H-pyrazol-3-yl}oxymethyl)phenyl)-N-methoxycarbamate,
- anilinopyrimidines, such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl) aniline,
- phenylpyrroles such as 4-(2,2-difluoro-1,3-benzodioxol-4-yl) pyrrole-3-carbonitrile,
- cinnamamides, such as 3-(4-chlorophenyl)-3-(3,4-dimethoxyphenyl)acryloylmorpholide, 3-(4-fluorophenyl)-3-(3,4-dimethoxyphenyl) acryloylmorpholide,
- and a variety of fungicides, such as dodecylguanidine acetate, 1-(3-bromo-6-methoxy-2-methylphenyl)-1-(2, 3,4-trimethoxy-6-methylphenyl)methanone, 3-[3-(3,5-dimethyl-2-oxycyclohexyl)-2-hydroxyethyl] glutarimide, hexachlorobenzene, methyl N-(2,6-dimethyophenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzohydryl alcohol, N-(3-chloro-2,6-dinitro-4-trifluoromethylphenyl)-5-trifluoromethyl-3-chloro-2-aminopyridine, 1-((bis-(4-fluorophenyl)methylsilyl)methyl)-1H-1,2,4-triazole, N,N-dimethyl-5-chloro-2-cyano-4-p-tolylimidazole-1-sulfonamide, 3,5-dichloro-N-(3-chloro-1-ethyl-1-methyl-2-oxopropyl)-4-methyl benzamide.

SYNTHESIS EXAMPLES

The procedures given in the synthesis examples below were used to obtain further compounds I by appropriate modification of the starting materials. The compounds obtained in this manner are listed in the tables that follows, together with physicl data.

Example 1

Preparation of 3,4-trimethoxy-1-methylxanthen-9-one [I-1]

Example 1a (1-(2,6-dichlorophenyl)-1-(2-hydroxy-3,4-dimethoxy-6-methylphenyl)methanone At 20–25° C., a solution of 52.4 g (0.25 mol) of o,o'-dichlorobenzoyl chloride in nitrobenzene was added to a solution of 40 g (0.3 mol) of aluminum trichloride in 400 ml of nitrobezene. After 30 min of stirring, 45.5 g (0.25 mol) of nitrobenzene. After 30 min of stirring, 45.5 g (0.25 mol) of trimethoxytoluene, dissolved in nitrobenzene, were added dropwise. After about two hours of stirring at 50° C., water was added and the mixture was then extracted twice with dichloromethane. The combined organic phases were dried and the solvent was removed. Silica gel chromatography (ethyl acetate/cyclohexane mixtures) gave 40.0 g of the title compound.

Example 1b

Cyclization to 3,4,8-trimethoxy-1-methylxanthen-9-one [I-1]

At about 0–5° C. under a protective atmosphere, 37.5 g (0.11 mol) of the benzophenone derivative from Example 1a in 100 ml of dimethoxyethane were added to a solution of 2.6 g (110 mol) of sodium in 50 ml of methanol. After about 72 hours of stirring at 80° C., the title compound was precipitated by adding a 1:1 mixture of water and ethyl acetate. 33.4 g (100% of theory) of product of m.p. 158° C. were isolated by filtration.

Example 2

Preparation of 5-bromo-3,4,8-trimethoxy-1,8-dimethylxanthen-9-one [I-2]

At about 0° C., 9.4 g (5.9 mmol) of bromine were added to a solution of 33.4 g of the xanthone from Example 1b in 100 ml of dichloromethane. After about 16 hours of stirring at 20–25° C., ice-water was added and the mixture was extracted with dichloromethane. The combined organic phases were washed with water and sat. sodium bicarbonate solution and dried. Removal of the solvent gave 2.1 g (5.5 mmol, 93% of theory) of the title compound.

Example 3

Preparation of 7-chloro-3,4-dimethoxy-1,8-dimethylxanthen-9-one [I-5]

Example 3a

Methyl-4-chloro-5-methylsalicylate

At 80° C., 9.9 g (73 mmol) of sulfuryl chloride were added dropwise to a solution of 11 g (66 mmol) of methyl o-methylsalicylate in 600 ml of glacial acetic acid. The solution was stirred at 100° C. for about eight hours and at about 20–25° C. for a further 12 hours. The reaction mixture was poured into water and then extracted with ethyl acetate. The combined organic phases were washed with water and dried, and the solvent was removed. This gave 12.85 g (64 mmol) of the title compound (97% of theory) which were used for the next step.

Example 3b 4-chloro-5-methyl-salicylic Acid 5.12 (128 mmol) of NaOH were added to a solution of 12.85 g (64 mmol) of the ester from Ex. 3a in 80 ml of water and 130 ml of ethanol, and the mixture was then refluxed for about 15 hours. The reaction mixture was poured into water and washed with ethyl acetate. Following phase separation, the aqueous phase was acidified and extracted with ethyl acetate. The combined organic phases were washed with water and dried, and the solvent was removed. This gave 10.4 g (55.8 mmol, 87% of theory) of the title compound as a yellow crystalline material.

Example 3c 3-chloro-6-(2,2-dimethylpropanyloxy)-2-methylbenzoic Acid 1.2 ml of pyridine and 1.62 g (13.48 mmol) of pivaloyl chloride were added to a solution of 2.35 g (12.6 mmol) of the acid from Ex. 3b in 30 ml of tetrahydrofuran,. After about 15 hours of stirring at about 20–25° C., the reaction mixture was poured into water and then extracted with ethyl acetate. The combined organic phases were dried and the solvent was removed. The residue gave 3.45 g (10% of theory) of the title compound.

Example 3d 4-chloro-3-methyl-2-[1-(2,3,4-trimethoxy-6-methyl phenyl)methanoyl]phenyl 2,2-dimethylpropionate 2.3 g (12.6 mmol) of trimethoxytoluene and 4 g of powdered $P_2O_5$ were added to a solution of 3.45 g (12.6 mmol) of the benzoic acid from Ex. 3c in 50 ml of dichloromethane ($CH_2Cl_2$). After about 15 hours of stirring at about 20–25° C., the reaction mixture was poured into water and then extracted with $CH_2Cl_2$. The combined organic phases were washed with water and dried, and the solvent was removed. The residue gave 4.9 g (89% of theory) of the title compound.

Example 3e

7-chloro-3,4-dimethoxy-1,8-dimethylxanthen-9-one [I-5]

15.7 g (148 mmol) of sodium bicarbonate were added to a solution of 22 g (50.6 mmol) of the pivaloyl derivative from Ex. 3d in 400 ml of methanol and 160 ml of water, and the mixture was relfuxed for about one hour and then stirred at about 20–25° C. for a further 15 hours. The reaction mixture was poured into water and extracted with ethyl acetate. The combined organic phases were washed with water and dried, and the solvent was removed. The residue was subjected to silica gel chromatography (methyl tert-butyl ether/hexane 1:20). The product fraction was freed from the solvent and digested with petroleum ether. This gave 0.41 g of the title compound of m.p. 101° C.

Example 4

Alternative Preparation of 7-chloro-3,4-dimethoxy-1,8-dimethylxanthen-9-one [I-5]

Example 4a

1-(3-chloro-6-hydroxy-2-methylphenyl)-1-(2,3,4-trimethoxy-6-methylphenyl)methanone 2 g (21 mmol) of $NaHCO_3$ were added to a solution of 2.8 g (6.44 mmol) of the compound from Ex. 3d in 60 ml of methanol and 20 ml of water, and the mixture was refluxed for 5 hours and then stirred at about 20–25° C. for 15 hours. The mixture was poured into water and extracted with ethyl acetate. The combined organic phases were washed with water and then with sat. $NaHCO_3$ solution and dried, and the solvent was removed. Following digestion with petroleum ether, the residue was filtered off. This gave 1.7 g (74% of theory) of the title compound.

Example 4b

7-chloro-3,4-dimethoxy-1,8-dimethylxanthen-9-one [I-5]

1.2 g (21.5 mmol) of KOH were added to a solution of 1.5 g (4.3 mmol) of the product from Ex. 4a in 15 ml of N-methylpyrrolidone and 30 ml of methanol, and the mixture was then refluxed for 5 hours. After cooling, the reaction mixture was poured into water and then extracted with dichloromethane. The combined organic phases were washed with water and dried. Removal of the solvent and chromatographic purification of the residue (methyl tert-butyl ether:hexane 1:9) gave 0.72 g of the title compound as colorless crystals of m.p. 101° C.

TABLE I

| No. | $R^1$ | $R^2$ | $R^3$ | $R^4$ | $(R^5)_n$ | Phys. data (m.p. [° C.]) |
|---|---|---|---|---|---|---|
| I-1 | $CH_3$ | $OCH_3$ | $OCH_3$ | $OCH_3$ | H | 158 |
| I-2 | $CH_3$ | $OCH_3$ | $OCH_3$ | $OCH_3$ | 5-Br | 162 |
| I-3 | $CH_3$ | $OCH_3$ | $OCH_3$ | $CH_3$ | 5-Br | 184 |
| I-4 | $CH_3$ | $OCH_3$ | $OCH_3$ | $CH_3$ | 7-Br | 190 |
| I-5 | $CH_3$ | $OCH_3$ | $OCH_3$ | $CH_3$ | 7-Cl | 180 |

Examples of the action against harmful fungi

The fungicidal action of the compounds of the formula I was demonstrated by the following tests:

The active compounds were prepared separately or jointly as a 10% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Wettol® EM (nonionic emulsifier based on ethoxylated castor oil) and diluted with water to the desired concentration.

Use example—activity against powdery mildew of wheat

Leaves of potted wheat seedlings of the cultivar "Kanzler" were sprayed to runoff point with an aqueous preparation of active compound which had been prepared from a stock solution of 10% of active compound, 63% of cyclohexanone and 27% of emulsifier. 24 hours after the spray coating had dried on, the leaves were dusted with spores of mildew of wheat (Blumeria graminis forma specialis tritici). The test plants were then placed in a greenhouse at 20–24° C. and 60 to 90% relative atmospheric humidity.

After 7 days, the extent of the mildew development was determined visually in % infection of the entire leaf area.

In this test, the plants which had been treated with 4 and 16 ppm of the compound I-5 showed an infection of not more than 3%, whereas the untreated plants were 90% infected.

We claim:

1. A xanthone derivative of the formula I

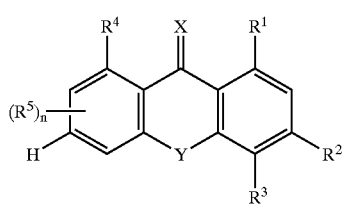

where the index and the variables are as defined below:
n is 0, 1 or 2;
$R^1$ is $C_1$–$C_4$-alkyl or $C_1$–$C_4$-haloalkyl;
$R^2$, $R^3$ independently of one another are hydrogen, $C_1$–$C_6$-alkoxy, $C_3$–$C_6$-alkenyloxy or $C_3$–$C_6$-alkynyloxy, or $R^2$ and $R^3$ together form an oxy-$C_1$–$C_4$-alkyleneoxy group which is unsubstituted or substituted by 1 to 4 of the following radicals; halogen, cyano, hydroxyl or $C_1$–$C_4$-alkyl;

$R^4$ is halogen, cyano, hydroxyl, amino, mercapto, $C_1$–$C_4$-alkyl, $C_1$–$C_4$-haloalkyl, $C_1$–$C_4$-alkoxy, $C_1$–$c_4$-haloalkoxy, $C_1$–$C_4$-alkylthio, $C_1$–$C_4$-haloalkylthio, $C_1$–$C_4$-alkylcarbonyloxy or $C_1$–$C_4$-alkylcarbonylthio;

$R^5$ is a group $R^4$, where the groups $R^5$ may be different if n=2;

X, Y independently of one another are oxygen or sulfur.

2. A compound of the formula I as claimed in claim 1 in which X and Y are oxygen.

3. A compound of the formula I as claimed in claim 1 in which $R^1$ is methyl.

4. A compound of the formula I as claimed in claim 1 in which $R^2$ and $R^3$ are methoxy, ethoxy, n- or isopropoxy or n-butoxy.

5. A compound of the formula I as claimed in claim 1 in which $R^4$ is methyl and $R^5$ is halogen.

6. A process for preparing compounds of the formula I as claimed in claim 1 where X is oxygen by condensing alkylbenzene derivatives of the formula II

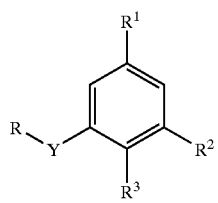

II in which R is a $C_1$–$C_4$-alkyl group and the other variables are as defined in formula I with salicylic acid derivatives of the formula III,

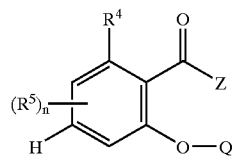

III in which Z is hydroxyl, halogen or $C_1$–$C_4$-alkoxy, Q is a protective group and $R^4$ and $(R^5)_n$ are as defined in formula I to give compounds of the formula IV,

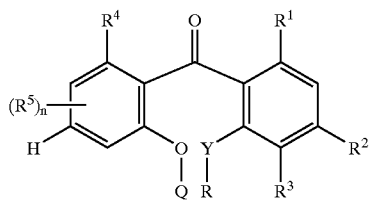

IV removal of Q and cyclization to give the compounds of the formula I.

7. A process for preparing compounds of the formula I as claimed in claim 1 where X and Y are oxygen and $R^4$ is hydroxyl, $C_1$–$C_4$-alkoxy or $C_1$–$C_4$-haloalkoxy by condensing alkylbenzene derivatives of the formula II.1,

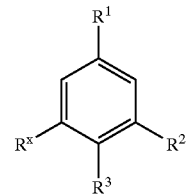

II.1 in which $R^x$ is $C_1$–$C_3$-alkoxy and benzoyl halides of the formula III.1

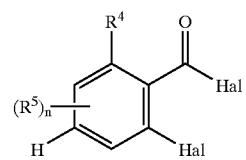

III.1 in which Hal is halogen to give compounds of the formula IV.1

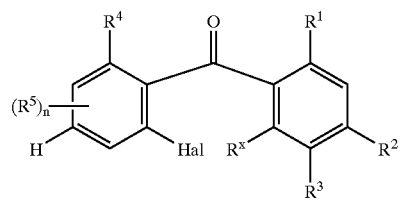

IV.1 and base-catalyzed cyclization of IV.1 in the presence of bases to give compounds of the formula I.

8. A composition suitable for controlling harmful fungi, which composition comprises a solid or liquid carrier and a compound of the general formula I as claimed in claim 1.

9. A process for controlling phytopathogenic harmful fungi, which comprises treating the fungi or the materials, plants, the soil or seeds to be protected against fungal attack with an effective amount of a compound of the general formula I as claimed in claim 1.

* * * * *